US011534562B2

(12) United States Patent
Güsson et al.

(10) Patent No.: US 11,534,562 B2
(45) Date of Patent: Dec. 27, 2022

(54) NASAL RINSING CAP FOR BOTTLES

(71) Applicant: CAPSTER OÜ, Saue (EE)

(72) Inventors: Mihkel Güsson, Tallinn (EE); Tarmo Härmaorg, Tallinn (EE); Veiko Liis, Tallinn (EE); Raivo Tamsalu, Keila (EE)

(73) Assignee: Capster OU, Saue (EE)

( * ) Notice: Subject to any disclaimer, the term of this patent is extended or adjusted under 35 U.S.C. 154(b) by 444 days.

(21) Appl. No.: 16/311,968

(22) PCT Filed: Jun. 20, 2017

(86) PCT No.: PCT/EE2017/000005
§ 371 (c)(1),
(2) Date: Dec. 20, 2018

(87) PCT Pub. No.: WO2017/220101
PCT Pub. Date: Dec. 28, 2017

(65) Prior Publication Data
US 2019/0184115 A1    Jun. 20, 2019

(30) Foreign Application Priority Data
Jun. 22, 2016   (EE) ................. U201600030

(51) Int. Cl.
*A61M 15/08*      (2006.01)
*A61M 3/02*       (2006.01)
(Continued)

(52) U.S. Cl.
CPC ............. *A61M 15/08* (2013.01); *A61H 35/04* (2013.01); *A61M 3/0262* (2013.01);
(Continued)

(58) Field of Classification Search
CPC .......... A61M 15/08; A61M 2210/0618; A61M 3/02; A61M 3/0262; A61M 3/0279;
(Continued)

(56) References Cited

U.S. PATENT DOCUMENTS 5,390,805 A    2/1995  Bilani et al.
6,907,879 B2   6/2005  Drinan et al.
(Continued)

FOREIGN PATENT DOCUMENTS

EP    0496892 A1 *  8/1992    ............ A61J 11/002
EP    0555623 A1    8/1993
(Continued)

OTHER PUBLICATIONS

International Search Report dated Oct. 4, 2017 in corresponding application PCT/EE2017/000005.

*Primary Examiner* — Benjamin J Klein
(74) *Attorney, Agent, or Firm* — Muncy, Geissler, Olds & Lowe, P.C.

(57) ABSTRACT

A nasal rinsing cap suitable for standard water bottle is disclosed. The body portion of the device can be attached to the top of the bottle. It has a cylindrical void matching the threaded portion of the bottle and a one-way fluid valve attached to another void extending from the cylindrical void and through the body portion. The body portion also includes a one-way air valve allowing the entry of air into the bottle. A top portion is removably or openably attached to the body portion. It has a tubular opening starting near the body portion and extending through the top portion. The top portion is configured so that it has a tip to be contacted with the user's nasal cavities. The top portion also has a pressure zone for closing the fluid valve by applying a pressure on it.

20 Claims, 6 Drawing Sheets

A-A

(51) Int. Cl.
*A61H 35/04* (2006.01)
*A61M 39/24* (2006.01)

(52) U.S. Cl.
CPC .......... *A61M 3/0279* (2013.01); *A61M 39/24* (2013.01); *A61M 2210/0618* (2013.01)

(58) Field of Classification Search
CPC .......... A61M 39/24; A61M 2039/2426; A61M 2039/2433; A61M 2039/244; A61M 2039/2446; A61M 3/0233; A61H 35/04; A61H 35/003; A61H 2205/023; A61J 11/002

See application file for complete search history.

(56) References Cited

U.S. PATENT DOCUMENTS

| | | |
|---|---|---|
| 8,092,434 B2 | 1/2012 | Harlan et al. |
| 9,168,204 B2 | 10/2015 | Pfenniger et al. |
| 2006/0253084 A1* | 11/2006 | Nordgren .............. F16K 15/147 604/247 |
| 2011/0319840 A1* | 12/2011 | Hair .................... A61M 3/0262 604/275 |
| 2012/0323221 A1 | 12/2012 | Gallo et al. |
| 2013/0158513 A1* | 6/2013 | Betz .................... A61M 3/0279 604/514 |

FOREIGN PATENT DOCUMENTS

| | | |
|---|---|---|
| WO | WO03066131 A2 | 8/2003 |
| WO | WO2008019271 A2 | 2/2008 |
| WO | WO2011020203 A1 | 2/2011 |

\* cited by examiner

A-A

C-C

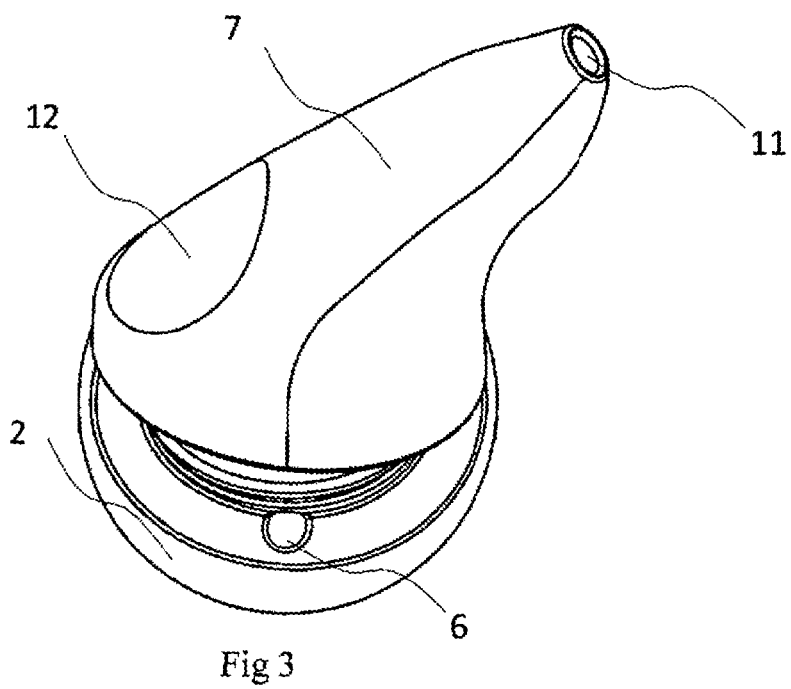
Fig 3
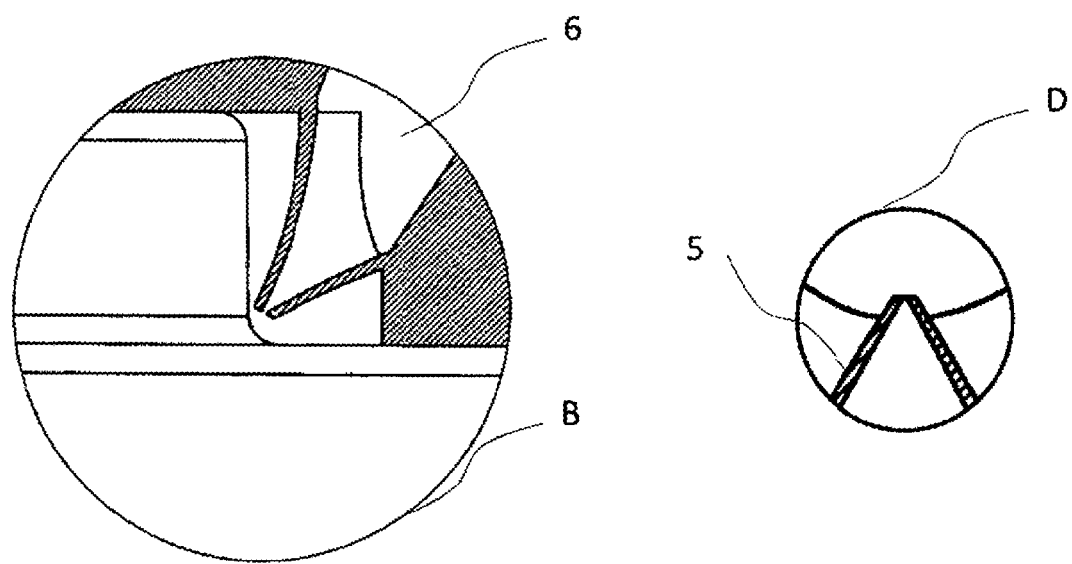
Fig 4
Fig 5

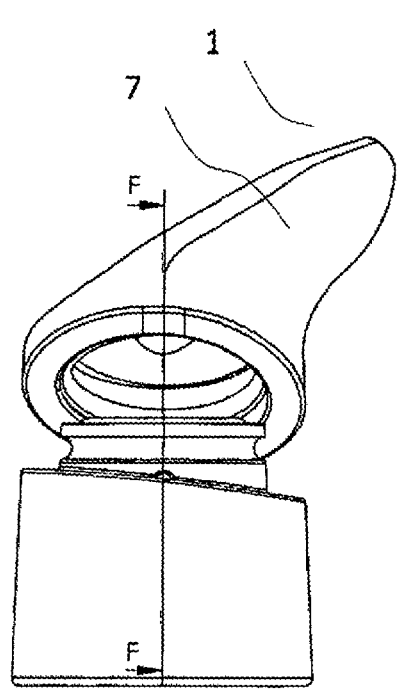
Fig 6A
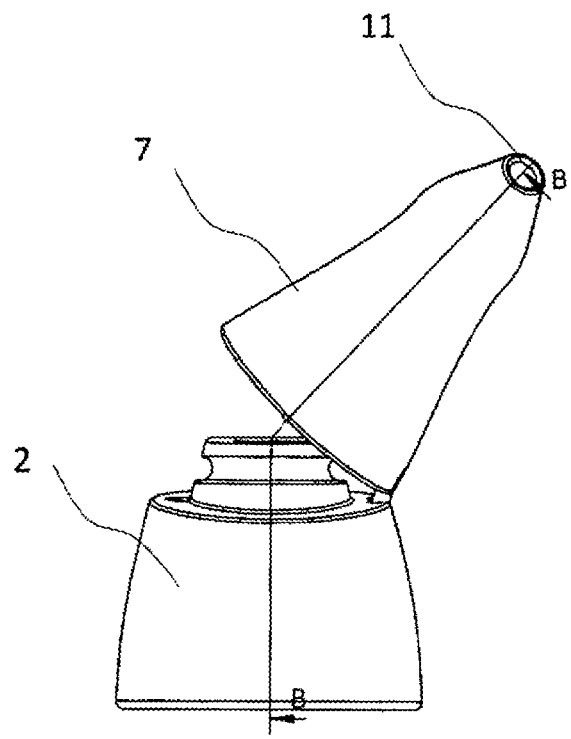
Fig 6B
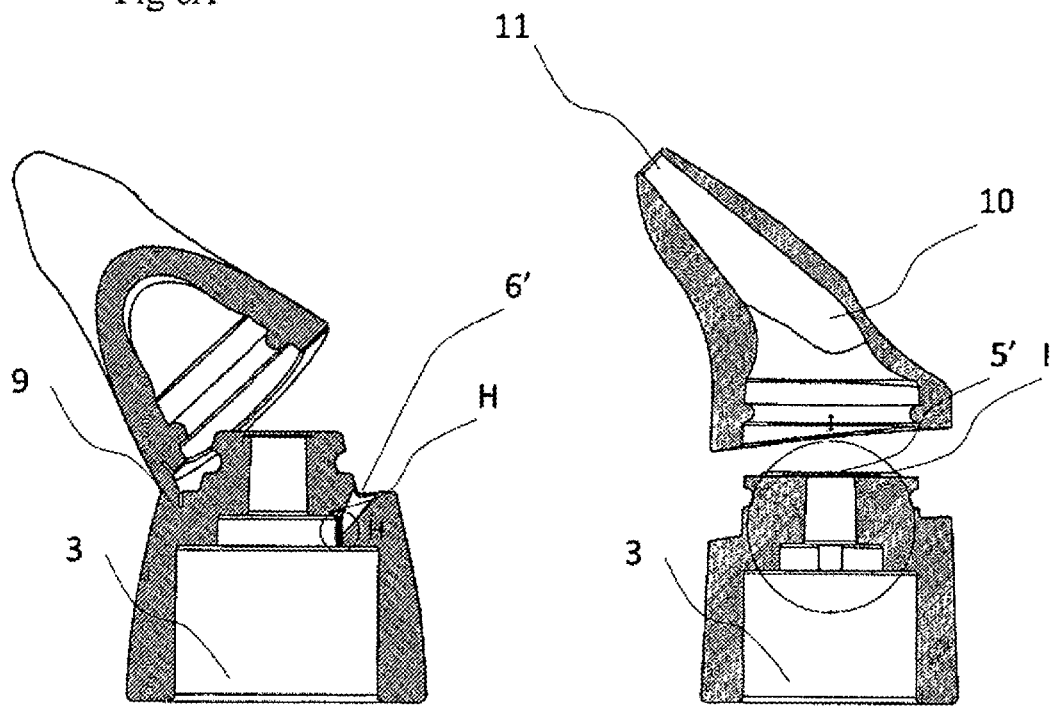
F-F
Fig 7A
B-B
Fig 7B

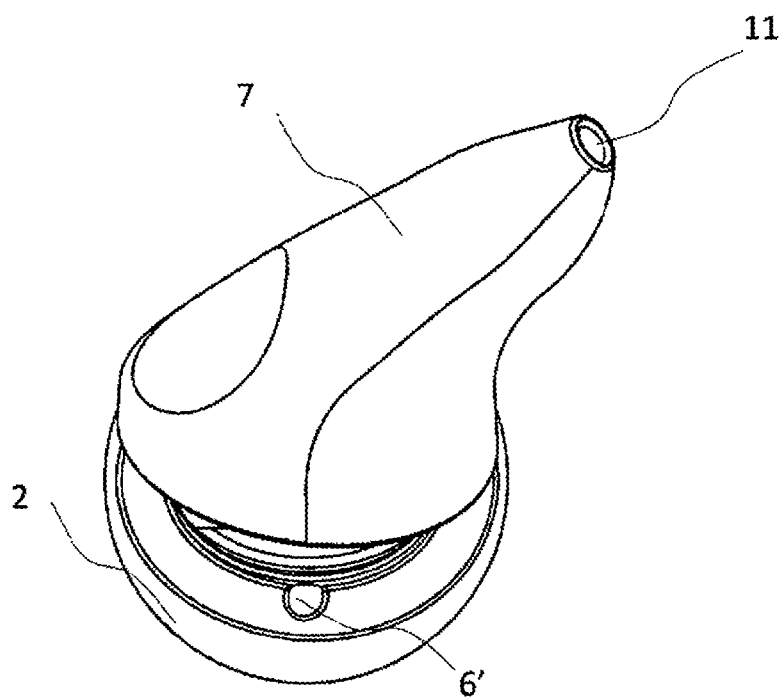
Fig 8
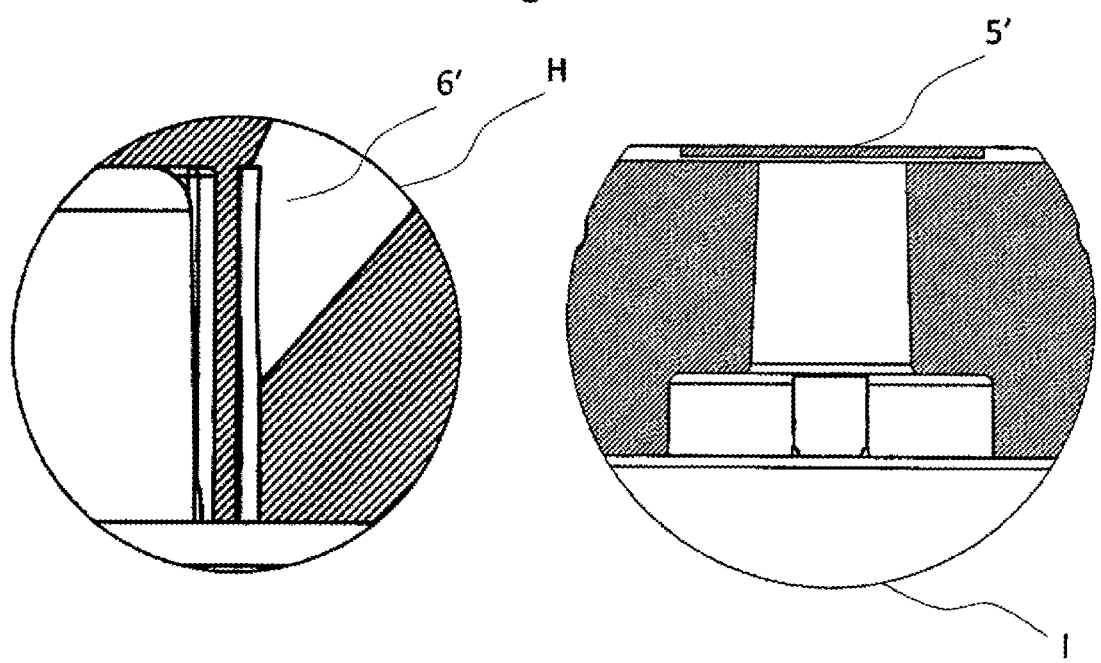
Fig 9
Fig 10

NASAL RINSING CAP FOR BOTTLES

This nonprovisional application is a National Stage of International Application No. PCT/EE2017/000005, which was filed on Jun. 20, 2017, and which claims priority to Estonian Patent Application No. U20160030, which was filed in Estonia on Jun. 22, 2016, and which are both herein incorporated by reference.

BACKGROUND OF THE INVENTION

Field of the Invention

The invention belongs to the field of healthcare and medical devices, more precisely to the field of devices for washing nasal passages and sinuses; particularly, to devices designed for use with regular, de facto standard plastic drinking bottles.

Description of the Background Art

U.S. Pat. No. 6,656,433, published on 2 Dec. 2003, which describes an adapter for mounting on drug vials of various types and sizes, is known from the state of the art.

US patent application no. US20120323221, published on 20 Dec. 2012, which describes an adapter cap that enables turning a plastic water or drinking bottle into a nasal washing device, is known from the state of the art. The described adapter cap may be equipped with a thread or partial thread. It may further be equipped with a solution for attachment to the collar of a plastic bottle or to the inside of a bottleneck. The device may be designed to fit on standard plastic bottles of different sizes. Such adapter caps may be sold with a packet of salt for the preparation of a saline solution for nasal rinsing. The tip of the adapter cap is suitable for insertion into the user's nose, and the cap has a through bore through which the liquid in a particular bottle can enter the user's nose. The cap is equipped with a vent tube, which extends to the bottom of the bottle it is attached to, and through which air enters the bottle when it is turned upside down.

The above device can be considered the closest equivalent known from the state of the art. The following issues are the weak points of the above device. The device is impractical for use due to both its shape and material (cast plastic, i.e. a solid material). The device is clumsy, particularly due to the vent tube's bad design. This invention is aimed at overcoming these and other technical and non-technical issues.

SUMMARY OF THE INVENTION

The objective of the invention is achieved by a nasal rinsing cap for bottles comprising a body part, which is attachable to the mouth of a bottle and has a cylinder-shaped vacuity in it for the threaded part of the mouth of a standard plastic drinking bottle, and a tubular vacuity extending from the cylinder-shaped vacuity through the body part to the end of the body part for discharging liquids from the bottle through the body part, wherein the tubular vacuity is equipped with a liquid valve to facilitate the flow of liquids through the cap out of the bottle as well as to prevent any backflow of liquids through the liquid valve back into the bottle; and the body part is equipped with an air valve to allow the entry of air into the bottle in the case of negative pressure when liquids are discharged, as well as to prevent any outflow of liquids through the air valve when the bottle is turned upside down or squeezed; and a top part, which can be removed or opened, is positioned on the body part, the top part comprising a tubular vacuity which runs through it, the tubular vacuity of the top part beginning from a point close to the tubular vacuity of the body part, extending through the top part and opening at the tip of the top part, wherein the top part is configured so that its tip can be made to touch the nasal cavity of the user, and a pressure region has been formed on the top part in order to close the liquid valve by putting pressure on the pressure region of the top part.

Preferably, the nasal rinsing cap is partially or fully made of a material which is sufficiently soft and elastic, such as the type of silicone used in the medical products or food industry, to facilitate its attachment to plastic bottles with different thread types. Preferably, the top part is made of a sufficiently soft and elastic material that enables forming an appropriate pressure region, which enables the user to close the liquid valve in the nasal rinsing cap by applying pressure on it. The liquid valve is preferably also made of such a material and configured so that the valve opens upon outflow of liquids from the bottle (due to the force of gravity, or pressure) but prevents any liquids from flowing back into the bottle. When pressure is applied on the liquid valve, the valve deforms, preventing liquids from flowing out of the bottle. The bottle recovers its former shape when pressure is no longer applied. The liquid valve may be integrated with the body part. Such a liquid valve is essentially a short tube, preferably a tube with a circular cross-section, which ends with a converging part, on top of which a slot is formed. In its normal state, the slot is tightly closed, but upon outflow of liquids it opens sufficiently to facilitate the through-flow of liquids, at the same time preventing liquids from running counter towards the inside of the bottle. When pressure is applied on the pressure region, the tube and its converging part deform sufficiently to prevent any liquids from moving out of the bottle through the tube. The valve may be integrated with the body part, designed as a single element with the body part, or installed in the body part as a separate assembly. Independently manufactured one-way valves, one-way cross-slit valves of appropriate dimensions, duckbill- or umbrella-type one-way valves may be used. The liquid valve may be produced of the same or different material as the body part, of a material that is of the same or different strength as the body part; the liquid valve may be produced of a material that is softer than the material of the body part. The air valve is analogous to the liquid valve, but its direction is opposite to that of the liquid valve.

In one preferred example embodiment, the nasal rinsing cap as a whole, i.e. its body part and the top part, are made of the same material. Silicone, which supports the presence and functioning of many of the aforementioned mechanisms in the device (the bottle collar joint, the ribs inside the cylinder, the seal between the two sides, the sockets of the valves, the mechanism of the button necessary for closing the valves) thanks to its elasticity, is preferably used. Furthermore, silicone is friendly and safe to and comfortable for the human body.

Silicone can be sterilised by means of boiling, for example, and silicone is resilient to strong, repeated physical stress, which is why products that are made of silicone have a long service life.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 represents a general view of the device depicted in FIG. 1A and FIG. 1B.

FIG. 4 represents an enlarged local view of area B marked in FIG. 2A.

FIG. 5 represents an enlarged local view of area D marked in FIG. 2B.

FIG. 6A and FIG. 6B represent a front and side view of the device according to another example embodiment.

FIG. 7A represents the F-F section of FIG. 6A.

FIG. 7B represents the B-B section of FIG. 6B.

FIG. 8 represents a top view of FIG. 7A.

FIG. 9 represents an enlarged local view of area H marked in FIG. 6A.

FIG. 10 represents an enlarged local view of area I marked in FIG. 6B.

FIGS. 11 to 16 represent a third example embodiment of the invention, wherein:

FIG. 11 represents a general view of the top part;

FIG. 12 represents a general view of the body part;

FIG. 13 represents a bottom view of the top part;

FIG. 14 represents an explanatory general view of the inside of the body part;

FIG. 15 represents a top view of the body part;

FIG. 16 represents a bottom view of the top part;

DETAILED DESCRIPTION

Figure 1A:
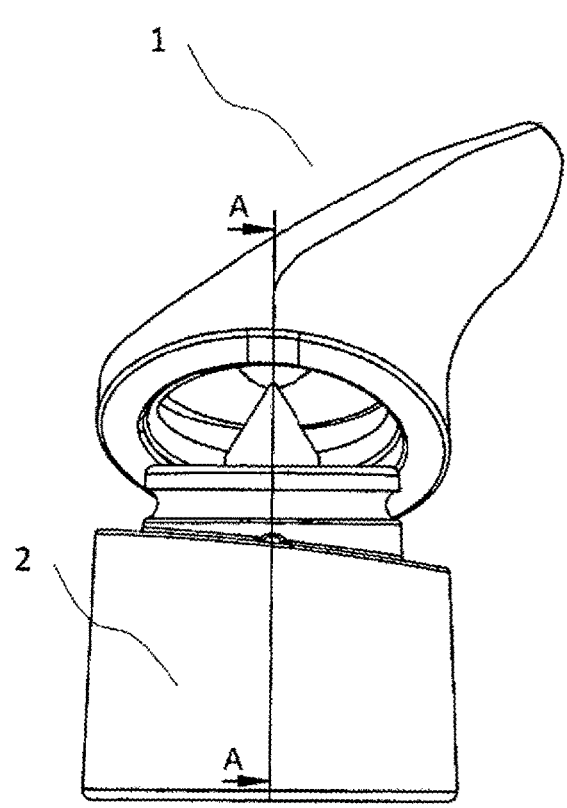
FIG. 1A and FIG. 1B represent a front and side view of the device according to one example embodiment.
Figure 1B:
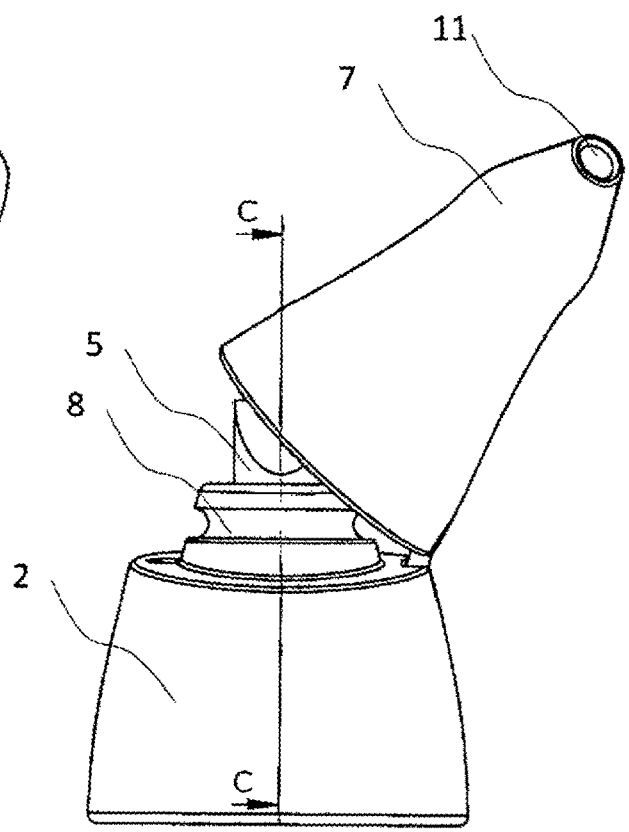
Figure 2A:
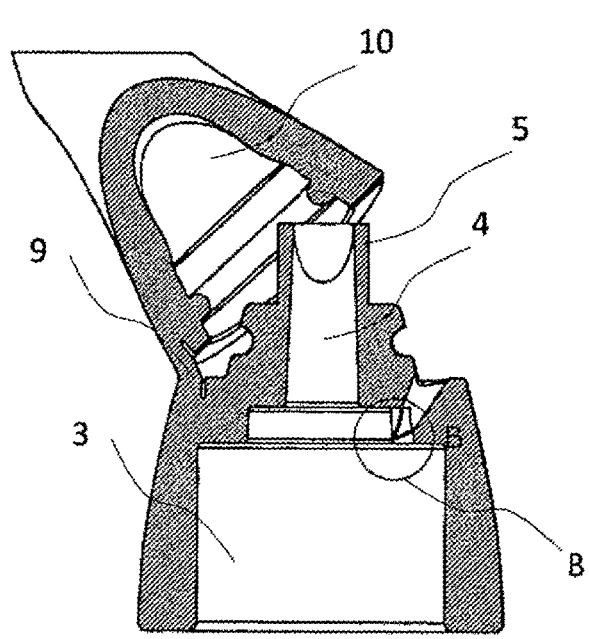
FIG. 2A represents the A-A section of FIG. 1A.
Figure 2B:
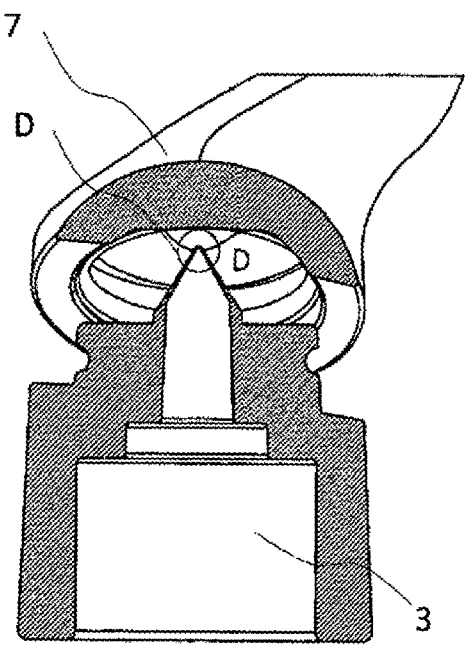
FIG. 2B represents the C-C section of FIG. 1B.

FIGS. 1 to 5 represent an example embodiment of the invention. The nasal rinsing cap 1 according to the example embodiment consists of a body part 2 installed on the mouth of a bottle, which has a cylinder-shaped vacuity 3 for bottle mouths as well as a tubular vacuity 4 extending from the cylinder-shaped vacuity to the tip of the body part for discharging liquids through the body part 2. There is a liquid cap 5 at the end of the vacuity 4 for controlling the discharge of liquids. The liquid valve 5 as per this example embodiment is depicted in FIG. 5 in enlarged form.

The liquid valve 5 (see the local view of area D in FIG. 5) prevents liquids from flowing back into the bottle. When moving out from the bottle, liquids open the valve. However, when liquids move from the outside into the bottle, they close the valve. The body part is also equipped with air valve 6, which is designed to allow the entry of air into the bottle, at the same time preventing any discharge of liquids from the bottle when the bottle is turned upside down, for example, e.g. when the bottle is used for nasal rinsing. The air valve 6 as per this example embodiment is depicted in view B in FIG. 4 in its enlarged form. In the case of negative pressure in the bottle when liquids are removed from the bottle through the tubular vacuity 4 and valve 5, air enters the bottle through the air valve 6 until the negative pressure is eliminated. A vacuum would be created inside the bottle without an air valve, and it would no longer be possible to squeeze the bottle, as it shrinks up as a result of negative pressure. At the same time, the air valve prevents liquids from flowing out of the bottle when the bottle is turned upside down or squeezed, for example. If there were just an opening instead of a liquid valve, any used water would get back inside the bottle, and the amount of negative pressure in the bottle, which would open the air valve, would also not be enough. All water would instead flow back into the bottle.

The air valve and liquid valve in combination therefore create a functioning system, which makes it possible to discharge liquids from the product by means of pumping movements as well as exert consistent pressure in case of counterpressure until the container that is used is empty, at the same time not interrupting contact with the object that uses the container, such as the human nose.

A removable top part 7 is mounted on the body part 2. According to this example embodiment, the top part is connected to the body part 2 by means of a coupling 8 and hinge 9. The top part includes a vacuity 10, which runs through it and ends with an opening 11 at the tip of the top part, which is designed for discharging liquids that exit the liquid valve 5 through the vacuity 10. The shape and dimensions of the top part are chosen so that the tip of the top part can be inserted in or brought into contact with the user's nasal cavity. A pressure region 12 has been formed on the top part, which can be used to close the liquid valve 5 by putting pressure on it by means of a finger (e.g. the user's thumb), for example when the bottle is turned upside down or shaken in order to prevent any liquid from flowing out of it.

The device 1 as a whole or parts of it, like the part surrounding the cylinder-shaped vacuity 3, the pressure region 12, or the valves, are made of an elastic, relatively soft material, such as silicone. In such a case, the cylinder-shaped part does not require a thread for attachment to the mouth of a bottle, which is why the device can be used on bottles with different thread types and sizes.

The tensile strength of the silicone used is between 2.4 and 5.5 MPa, its compressive strength 10 to 30 MPa, and its elastic limit 2.4 to 5.5 MPa.

The primary application of the device is to facilitate nasal rinsing by inserting the opening 11 of the top part 7 in the user's nasal cavity or bringing it into contact with the nasal cavity.

The device can also be used as a bottle cap.

The device may be manufactured as a single piece, but the user should be able to open in the middle to clean and rinse the device and its mechanisms as well as to sterilise the device. The body part and top part of the device may also be manufactured as separate pieces.

FIGS. 6 to 10 represent another example embodiment of the invention. The nasal rinsing cap 1 according to the example embodiment also consists of a body part 2 installed on the mouth of a bottle, which has a cylinder-shaped vacuity 3 for the bottle mouths as well as a tubular vacuity 4 extending from the cylinder-shaped vacuity to the tip of the body part for discharging liquids through the body part 2. There is a liquid valve with an alternative design 5' at the end of the vacuity 4 for controlling the discharge of liquids. FIG. 10 represents an enlarged view of the liquid valve 5'. The liquid valve is made up of a thin, leaf-shaped element (tongue), which is partially attached to the body part at the end of the vacuity. The body part is also equipped with an air valve 6', which is designed to allow the entry of air into the bottle, at the same time preventing any discharge of liquids from the bottle when the bottle is turned upside down, for example. FIG. 9 represents an enlarged view of the air valve 6'.

Figure 18:
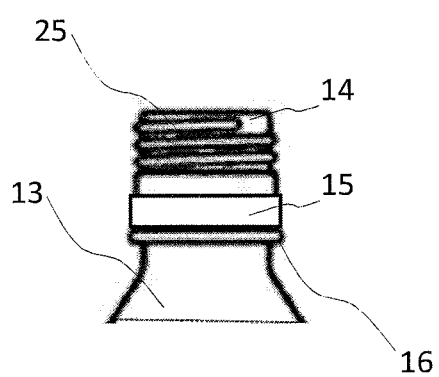
FIG. 18 represents the top of a liquid bottle to which nasal rinsing caps according to the invention are attached.
Figure 13:
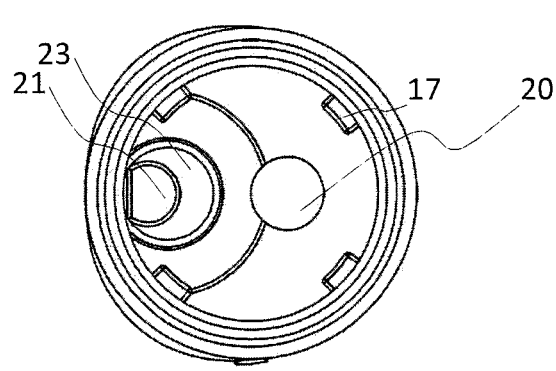
Figure 15:
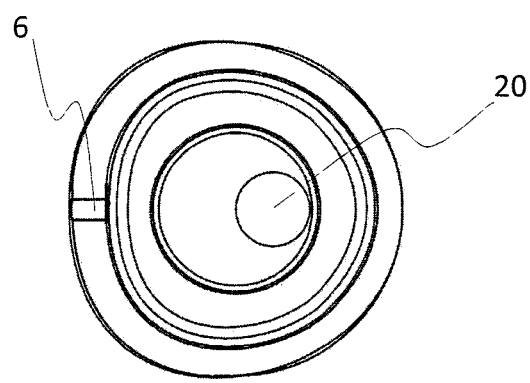

FIGS. 11 to 17 represent a third example embodiment of the invention, which is the preferred embodiment. The nasal rinsing cap 1 according to the example embodiment also consists of a body part 2 installed on the mouth 14 of a regular water bottle 13 (see FIG. 18), which has a cylinder-shaped vacuity 3 for bottle mouths as well as a tubular vacuity 4 extending from the cylinder-shaped vacuity to the tip of the body part for discharging liquids through the body part 2. There is a groove 15 for bottle collars 16 in the body part, enabling the formation of a tight connection between the nasal rinsing cap and a particular bottle collar. This furthermore provides universal suitability, as the collars of standard bottles have the same dimensions.

There are longitudinal ribs 17 inside the body part, and a vacuity 18 has been formed between the end of the ribs and the groove 15, in which the cap ring 19 that remains attached to the bottle when a water bottle is opened fits (removing the cap ring when opening a bottle is an inconvenient extra procedure, and it is nearly impossible without extra means). The number of longitudinal ribs is preferably two to six, more preferably three to four.

The longitudinal ribs 17 facilitate attachment of the threaded part of a bottle mouth 25 to cylinders with a larger diameter. Thanks to the ribs, the threaded part of a particular bottle does not shake inside the body part, and the body part is fastened to the bottle collar 16. Alternatively, the inside of the body part may be designed with a smaller diameter in the upper part. However, a design with ribs is preferred, which makes it possible to save on materials, manufacture a lighter product and/or shorten the production time of the product (e.g. when the product requires hardening).

The body part includes an opening 20 for a liquid valve. The liquid valve is produced as a separate element and attached to the body part during the construction process.

An opening 21 for an air valve opens into the inside of the body part, linking the inside of the body part and the external environment by means of a channel 22. The air valve is also produced as a separate element and attached to the body part during the construction process.

Independently manufactured one-way valves, one-way cross-slit valves of appropriate dimensions, duckbill or umbrella-type one-way valves may be used. The liquid valve may be produced of the same or different material as the body part, of a material that is of the same or different strength as the body part; the liquid valve may be produced of a material that is softer than the material of the body part. The air valve is analogous to the liquid valve, but its direction is opposite to that of the liquid valve.

As the valves are separated from each other by a partition wall 23, the nasal rinsing cap need not be removed from the nose during rinsing. The user squeezes the bottle, releases it, and repeats the procedure, as a result of which liquid is discharged from the tip of the device. Upon release of the bottle, air enters the bottle through the other channel due to vacuum, making it possible to squeeze the bottle again, which has been refilled with air.

Figure 11:
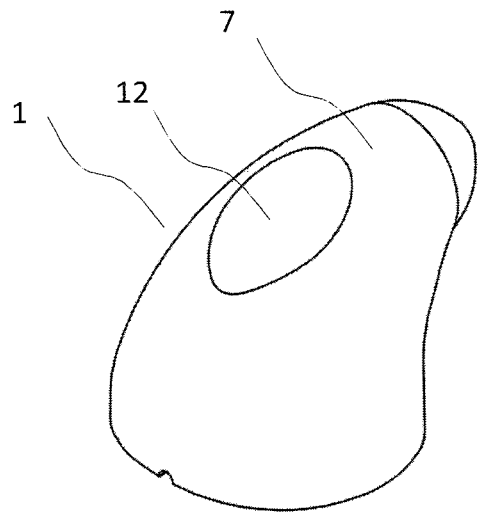
Figure 14:
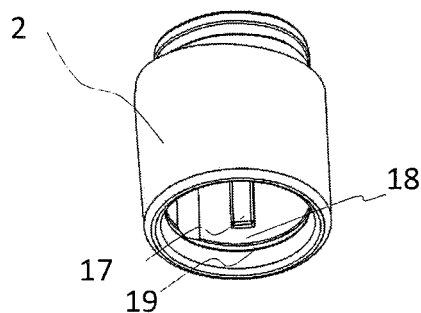
Figure 12:
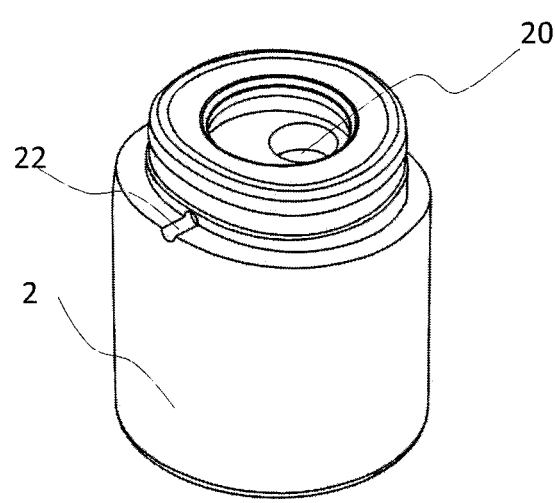
Figure 16:
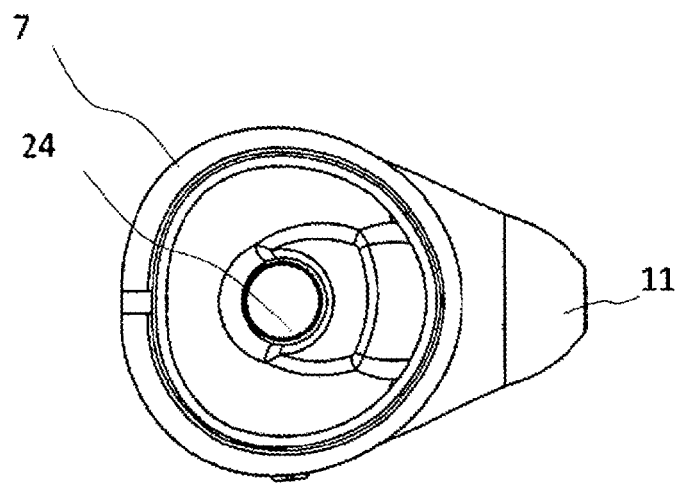
Figure 17:
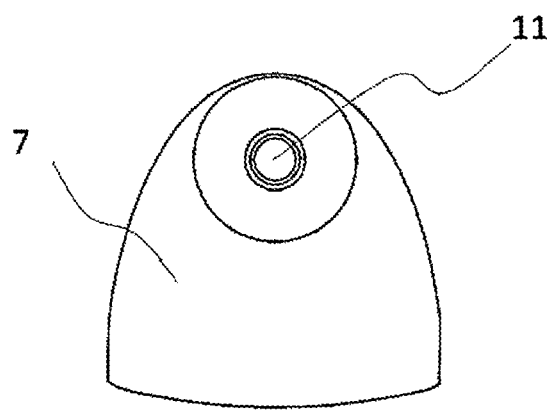
FIG. 17 represents a side view of the top part.

FIGS. 11, 16, 17 represent the top part 7. The top part includes a cylinder-shaped element 24, which connects the pressure region 12 with the liquid valve so that when pressure is applied on the pressure region, the liquid valve closes, preventing liquids from exiting the opening 11 of the nasal rinsing cap at the tip of the top part.

The shape of the nasal rinsing cap is preferably such that the bottle and the nosepiece are approximately at a 90-degree angle. This shape enables the user to hold the bottle in the same position during rinsing (upside down), which ensures that the liquid always stays on the side of the nasal rinsing cap of the bottle, and that liquid, not air, is discharged from the bottle when pressure is applied.

Before the device is used, a dry mix is dissolved in the bottle to get a specific quantity, such as 0.5 litres of physiological salt solution. The bottle is shaken to ensure that the mix is dissolved in it, but the solution may burst out of the bottle when the bottle is shaken. For this purpose, the top part has a pressure region, which ensures that the valve remains closed when pressure is applied on it with one's thumb.

In addition to continued pumping of liquids into the user's nasal cavity, the device can also be used as an air pump. Air moves in only one direction because the backflow valve of the device prevents air from escaping the device, and the device need not be detached from the item that is pumped. Therefore, the item that is being pumped can be pumped by applying repeated pumping motions without detaching the item that is being pumped from the device.

Which is to say that the device as per the invention is a positive displacement pump which can be used to pump both air and liquids.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A nasal rinsing cap for bottles comprising a body part, which is mountable to a mouth of a bottle and has a cylinder-shaped vacuity in it for a threaded part of the mouth of the bottle, and a tubular vacuity extending from the cylinder-shaped vacuity through the body part to an end of the body part for discharging liquids from bottles connected to the nasal rinsing cap when it is used, wherein the tubular vacuity is equipped with a liquid valve to facilitate a flow of liquids through the cap out of the bottle as well as to prevent any backflow of liquids back into the bottle; and the body part is equipped with an air valve to allow an entry of air into the bottle upon occurrence of negative pressure in it as well as to prevent any outflow of liquids when the bottle is turned upside down or squeezed; and a top part, which can be removed or opened, is positioned on the body part, the top part comprising a tubular vacuity which runs through it, the tubular vacuity of the top part beginning from a point adjacent the tubular vacuity of the body part, extending through the top part and opening at a tip of the top part, wherein the top part is configured so that its tip can be inserted in a nasal cavity of the user, and a pressure region has been formed on the top part to close the liquid valve by putting pressure on the pressure region of the top part by means of a finger, wherein the body part and the top part are made of an elastic material, and wherein the liquid valve and the air valve of the nasal rinsing cap are made of silicon.

2. A nasal rinsing cap according to claim 1, wherein the body part is made of a soft, elastic material to facilitate attachment to plastic bottles of different thread types.

3. A nasal rinsing cap according to claim 1, wherein there is a hollow groove in the body part for a collar of the bottle.

4. A nasal rinsing cap according to claim 1, wherein there is a vacuity in the body part for a ring of a screw cap.

5. A nasal rinsing cap according to claim 1, wherein the elastic material of the top part facilitates the creation of an appropriate pressure region that allows the user to close the liquid valve by applying pressure on it.

6. A nasal rinsing cap according to claim 1, wherein the liquid valve is in its open position when liquids move outwards and in its closed position when liquids move backwards, and the liquid valve is in a deformed position when pressure is applied on the pressure region of the top part, preventing any backflow of liquids.

7. A nasal rinsing cap according to claim 6, wherein the liquid valve is formed of a short tube with a convergent tip, which has a slot in it, which is tightly sealed in its normal position but opens enough to allow liquids to flow through when liquids move in a direction toward the tip of the top part, at the same time preventing any counterdirectional movement of liquids towards an inside of the bottle.

8. A nasal rinsing cap according to claim 1, wherein the liquid valve is designed as a separate part independent of the body part and attached to an opening in the body part during design.

9. A nasal rinsing cap according to claim 1, wherein the air valve is designed as a separate part independent of the body part and attached to an opening in the body part during design.

10. A nasal rinsing cap according to claim 1, wherein the nasal rinsing cap functions as a positive displacement pump when installed on the bottle.

11. A nasal rinsing cap according to claim 1, wherein the top part comprises a cylinder-shaped element, which connects the pressure region with the liquid valve so that when pressure is applied on the pressure region, the liquid valve closes.

12. A nasal rinsing cap according to claim 1, wherein the liquid valve is designed as a single element together with the body part.

13. A nasal rinsing cap according to claim 1, wherein the air valve is designed as a single element together with the body part.

14. A nasal rinsing cap according to claim 1, wherein the nasal rinsing cap comprises two pieces or four pieces.

15. A nasal rinsing cap according to claim 1, wherein the body part and the top part are made of silicone.

16. A nasal rinsing cap according to claim 1, wherein the elastic material has a compressive strength of 10 MPa to 30 MPa.

17. A nasal rinsing cap according to claim 1, wherein the elastic material has an elastic limit of 2.4 MPa to 5.5 MPa.

18. A nasal rinsing cap according to claim 1, wherein the nasal rinsing cap comprises one piece.

19. A nasal rinsing cap according to claim 1, wherein the nasal rinsing cap comprises not more than four pieces.

20. A nasal rinsing cap for bottles comprising a body part, which is mountable to a mouth of a bottle and has a cylinder-shaped vacuity in it for a threaded part of the mouth of the bottle, and a tubular vacuity extending from the cylinder-shaped vacuity through the body part to an end of the body part for discharging liquids from bottles connected to the nasal rinsing cap when it is used,
wherein the tubular vacuity is equipped with a liquid valve to facilitate a flow of liquids through the cap out of the bottle as well as to prevent any backflow of liquids back into the bottle; and the body part is equipped with an air valve to allow an entry of air into the bottle upon occurrence of negative pressure in it as well as to prevent any outflow of liquids when the bottle is turned upside down or squeezed; and a top part, which can be removed or opened, is positioned on the body part, the top part comprising a tubular vacuity which runs through it, the tubular vacuity of the top part beginning from a point adjacent the tubular vacuity of the body part, extending through the top part and opening at a tip of the top part, wherein the top part is configured so that its tip can be inserted in a nasal cavity of the user, and a pressure region has been formed on the top part to close the liquid valve by putting pressure on the pressure region of the top part by means of a finger, and
wherein the top part comprises a cylinder-shaped element, which connects the pressure region with the liquid valve so that when pressure is applied on the pressure region, the liquid valve closes.

* * * * *